United States Patent
Suprise et al.

[11] Patent Number: 5,899,896
[45] Date of Patent: * May 4, 1999

[54] ABSORBENT ARTICLE WITH FASTENING SYSTEM TO PREVENT DROOPING

[75] Inventors: Jody Dorothy Suprise, Neenah; Georgia Lynn Zehner, Larsen; Paulette Mary Rosch, Sherwood, all of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/148,101

[22] Filed: Nov. 2, 1993

[51] Int. Cl.⁶ .................................................. A61F 13/15
[52] U.S. Cl. .......................................... 604/391; 604/358
[58] Field of Search ................................... 604/358, 386, 604/387, 389, 390, 393, 400, 391, 385.2, 385.1

[56] References Cited

U.S. PATENT DOCUMENTS

| | | | |
|---|---|---|---|
| 219,820 | 9/1879 | Kohl . | |
| 1,122,988 | 12/1914 | Myers . | |
| 1,163,793 | 12/1915 | Taylor et al. . | |
| 1,188,223 | 6/1916 | Uyeda . | |
| 1,288,848 | 12/1918 | Dudley . | |
| 2,516,951 | 8/1950 | Brink | 128/287 |
| 2,545,761 | 3/1951 | Brink | 128/287 |
| 2,575,054 | 11/1951 | Gowdy | 128/287 |
| 3,494,361 | 2/1970 | Thivat | 128/287 |
| 3,618,608 | 11/1971 | Brink | 128/287 |
| 3,902,236 | 9/1975 | Deem | 29/256 |
| 4,076,663 | 2/1978 | Masuda et al. | 260/17.4 GC |
| 4,149,335 | 4/1979 | Duescher | 43/42.53 |
| 4,286,082 | 8/1981 | Tsubakimoto et al. | 526/240 |
| 4,336,803 | 6/1982 | Repke | 128/287 |
| 4,555,244 | 11/1985 | Buell | 604/392 |
| 4,573,987 | 3/1986 | Lamb, Jr. | 604/378 |
| 4,589,878 | 5/1986 | Mitrani | 604/392 |
| 4,617,022 | 10/1986 | Pigneul et al. | 604/391 |
| 4,661,102 | 4/1987 | Shikata et al. . | |
| 4,704,116 | 11/1987 | Enloe | 604/385 A |
| 4,753,650 | 6/1988 | Williams | 604/389 |
| 4,798,603 | 1/1989 | Meyer et al. | 604/378 |
| 4,895,568 | 1/1990 | Enloe | 604/385.2 |
| 4,938,754 | 7/1990 | Mesek | 604/385.2 |
| 4,978,345 | 12/1990 | Holliday et al. | 604/384 |
| 4,988,346 | 1/1991 | Pfefferkorn | 604/389 |
| 5,055,103 | 10/1991 | Nomura | 604/385.2 |
| 5,062,839 | 11/1991 | Anderson | 604/385.1 |
| 5,147,343 | 9/1992 | Kellenberger | 604/368 |
| 5,176,671 | 1/1993 | Roessler | 604/391 |

FOREIGN PATENT DOCUMENTS

| | | |
|---|---|---|
| 0528282A2 | 2/1993 | European Pat. Off. . |
| 0532034A3 | 3/1993 | European Pat. Off. . |
| 3423644A1 | 1/1986 | Germany . |

Primary Examiner—Robert A. Clarke
Assistant Examiner—Dennis Ruhl

[57] ABSTRACT

The present invention is directed to an absorbent article which is configured to prevent drooping and to improve fit. The article comprises attachment means for attaching the article about the waist of a wearer such that attachment points are located on the sides of the article and behind a transverse center plane of the article.

31 Claims, 4 Drawing Sheets

ABSORBENT ARTICLE WITH FASTENING SYSTEM TO PREVENT DROOPING

BACKGROUND OF THE INVENTION

The present invention relates to absorbent articles. Specifically, the present invention relates to a fastening system for an absorbent article which helps prevent drooping of the articles.

Disposable absorbent articles, such as disposable diapers, training pants, adult incontinent garments, and the like, are known. Disposable diapers and adult incontinent garments often comprise a two-dimensional structure which is placed between the legs of a wearer and held in position through a wide variety of known fastening means. Examples of known fastening means are adhesive tapes, hook-and-loop type fasteners, belts, straps, and the like.

In the past, particularly in the case of infant diapers, known fastening means generally involve overlapping a rear ear portion of the diaper onto the front portion of the diaper where it is attached through the use of, for example, adhesive tapes. While a generally acceptable fit can be obtained with known fastening means, it is not unusual for infant diapers to sag or droop in the front portion of the diaper due to movements by the infant. In an attempt to lessen this drooping, waist elastics have been added to infant diapers in order to maintain a tighter fit about the waist of an infant and to prevent drooping in the front portion of the diaper. Again, the presence of waist elastics has been found to help obtain a better fit and to prevent drooping. Nonetheless, current fastening systems still allow for a degree of drooping and an associated ill-fitting appearance in infant diapers. It is, therefore, desired to provide an absorbent article having a fastening system which helps prevent drooping.

SUMMARY OF THE INVENTION

The present invention is directed to a disposable absorbent article. The article defines a front portion, a rear portion, and a crotch portion connecting the front and rear portions. The crotch portion has opposed longitudinal side edges. The article comprises an outer cover, a liquid-pervious body-side liner, and an absorbent material located between the outer cover and the body-side liner. A pair of opposed ears are located on the front portion and/or the rear portion and are adapted, in use, to overlap with the rear portion or front portion, respectively, of said article. The article further comprises attachment means for attaching said overlapped portions of said ears to said rear or front portion to form attachment points located on each side of the article. The attachment points are located on each side of the article behind a transverse center plane of said article. The article further comprises a waist elastic member attached to at least one of the front or rear portions of the article and further includes leg elastic members attached to the crotch portion adjacent the opposed longitudinal side edges.

In a preferred embodiment, the present invention is directed to a disposable absorbent article defining a front portion, a rear portion, and a crotch portion connecting the front and rear portions. The crotch portion has opposed longitudinal side edges. The article comprises an outer cover, a liquid-pervious body-side liner, and an absorbent material located between the outer cover and the body-side liner. A pair of opposed ears are attached to the front portion. The ears are adapted so that, in use, they overlap with the rear portion of the article. The hook members of a hook-and-loop fastener are attached to the ears. The loop members of a hook-and-loop fastener are attached to the outer cover in the rear portion and are configured to releasably engage with the hook members to form attachment points. At least some, and preferably all, attachment points are located behind a transverse center plane of said article and within about 2.5 inches (6.4 centimeters) of said transverse center plane. The article further comprises a waist elastic member attached to said front and said rear portions and separate leg elastic members attached to said crotch portion adjacent said opposed longitudinal side edges.

DETAILED DESCRIPTION OF THE PREFERRED EMBODIMENTS

The present invention relates to disposable absorbent articles. As used herein, the term "disposable absorbent article" refers to articles which absorb and contain body exudates and which are intended to be discarded after a limited period of use. The articles are not intended to be laundered or otherwise restored for reuse. The articles can be placed against, or in proximity to, the body of the wearer to absorb and contain various exudates discharged from the body. While the present description will be made in the context of a diaper article, it should be understood that the present invention is also applicable to other disposable personal care absorbent articles, such as adult incontinence garments, children's training pants, and the like.

Figure 1:
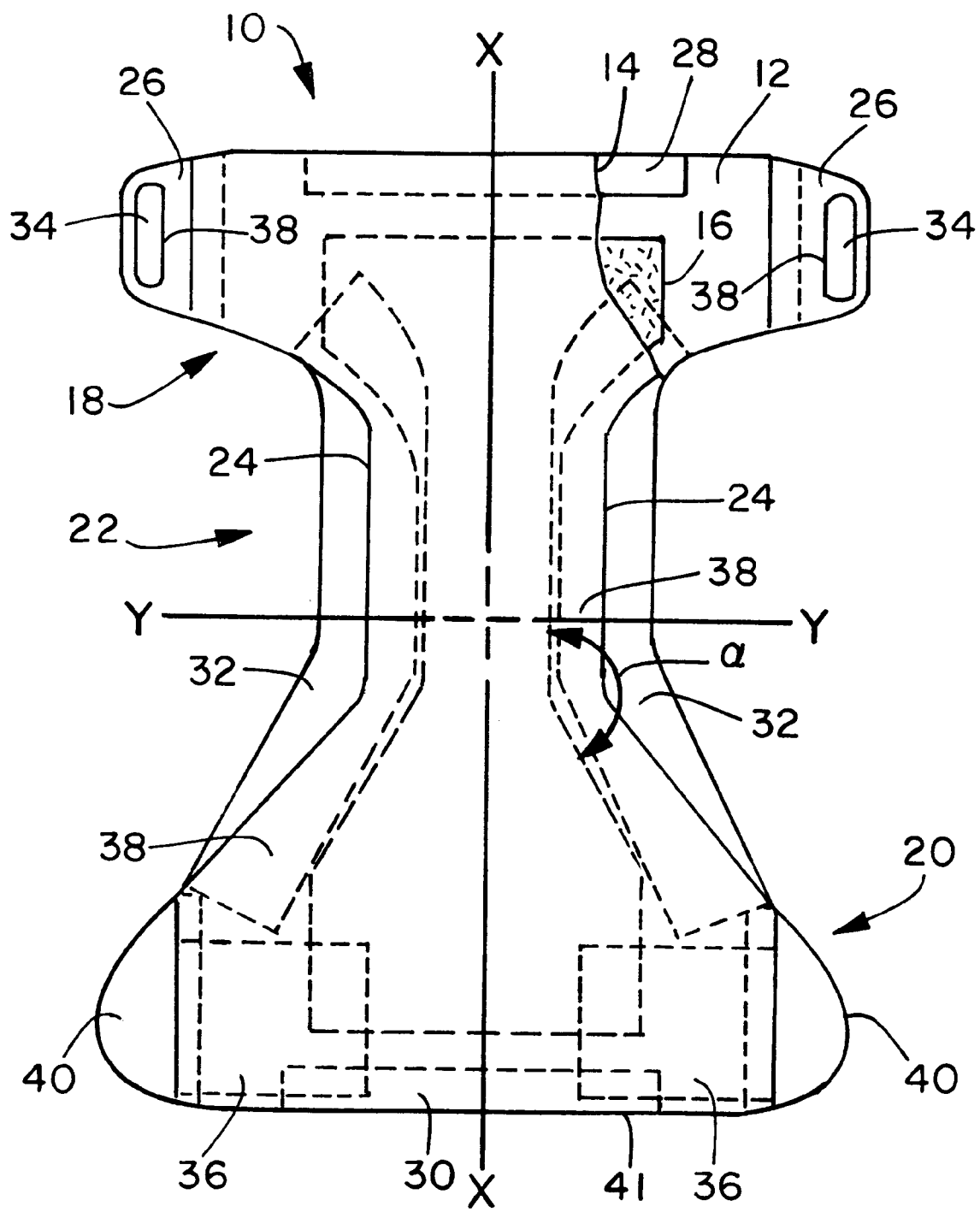
FIG. 1 is a plan view of a first embodiment of a disposable diaper according to the present invention.

Referring to the figures therein like numbers represent like elements, FIG. 1 illustrates an absorbent article such as a diaper 10, including an outer cover 12 and a liquid-pervious body-side liner 14 which is disposed in facing relation with the outer cover 12. An absorbent material 16 is disposed between the outer cover 12 and the body-side liner 14. The diaper 10 defines a front portion 18, a rear portion 20, and a crotch portion 22 connecting the front and rear portions. The crotch portion has opposed longitudinal side edges 24.

A pair of opposed ears 26 are located on the front portion of the diaper 10. The ears are adapted, in use, to overlap with the rear portion 20 of the diaper.

The diaper further comprises a front waist elastic member 28 attached to the front portion 18 and rear waist elastic member 30 attached to the rear portion 20. Leg elastic members 32 are attached to the crotch portion 22 of diaper 10 adjacent the opposed longitudinal side edges 24. The ears 26 comprise a first mechanical fastener, such as hook members 34, which is adapted to releasably engage with a second mechanical fastener, such as loop members 36. The hook members 34 attach to the inner body-facing side of the ears 26, while the loop members 36 are attached to the opposite, outer surface of the outer cover 12.

As will be explained in greater detail below, the ears 26 are adapted, in use, to overlap with the rear portion of the diaper. The hook members 34 and loop members 36 are thus brought into contact to form attachment points. As used herein, the term "attachment points" refers to the points at which the front portion is releasably attached to the rear portion of the absorbent article. Those skilled in the art will recognize that the attachment points will generally not be a single point but may, for example, be a rectangular area, a circular area, an elliptical area, or just about any other geometric form. In the embodiment illustrated in FIG. 1, the front portion would be attached to the rear portion over an area of attachment points which generally corresponds to the area containing hook members 34. At least some, and preferably all, of the attachment points are located on the side of the absorbent article behind a transverse center plane of the article.

The body-side liner 14 presents a body-facing surface which is compliant, soft-feeling, and non-irritating to the wearer's skin. Further, body-side liner 14 may be less hydrophilic than the absorbent material 16 and is sufficiently porous to be liquid pervious, permitting liquid to readily penetrate through its thickness. A suitable body-side liner 14 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The body-side liner 14 is typically employed to help isolate the wearer's skin from liquids held in the absorbent material 16.

Various woven and nonwoven fabrics can be used for body-side liner 14. For example, the liner may be composed of a meltblown or spunbonded web of polyolefin fibers. The body-side liner may also be a bonded-carded web composed of natural and synthetic fibers. For the purposes of the present description, the term "nonwoven web" shall mean a web of material which is formed without the aid of a textile weaving or knitting process.

The body-side liner may be composed of a substantially hydrophobic material, and the hydrophobic material may optionally be treated with a surfactant or otherwise processed to impart a desired level of wettability and hydrophilicity. In a particular embodiment of the present invention, body-side liner 14 is a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant, such as Triton X-102 surfactant.

The outer cover 12 may be composed of a liquid-permeable material but, preferably, comprises a material which is configured to be substantially impermeable to liquids. For example, a typical outer cover can be manufactured from a thin plastic film or other flexible, liquid-impermeable material. Outer cover 12 generally prevents the exudates contained in the absorbent material 16 from wetting articles, such as bed sheets and overgarments, which contact the diaper 10. In a particular embodiment of the present invention, the outer cover 12 is a polyethylene film having a thickness of from about 0.012 millimeter (0.5 mil) to about 0.051 millimeter (2.0 mils). In a preferred embodiment, the outer cover is a film having a thickness of about 1.25 mils.

In an alternative preferred embodiment of the present invention, the outer cover 12 is a stretch thermal laminate comprising a 0.6 mil (0.015 millimeter) polypropylene blown film and a 0.7 ounce per square yard (23.8 grams per square meter) polypropylene spunbond material. The spunbond material is composed of about 2.0 denier fibers. The stretch thermal laminate is formed by stretching the polypropylene film, in one direction, until it is extended by 25 percent. The spunbond polypropylene is then brought into face-to-face contact with the stretched, polypropylene film. The polypropylene film and spunbond material are then thermally bonded together at spaced intervals. The resulting laminate has a plurality of separate and distinct bond sites with an overall bond area of about 13 percent per unit area. After the film and spunbond material are laminated to one another, the laminate is allowed to relax. The film layer retracts about 10 percent, thereby leaving the film permanently deformed to a length of about 15 percent greater than its original length. The process for forming the stretch thermal laminate is described in greater detail in commonly-owned copending U.S. patent application Ser. No. 07/997,800, filed Dec. 29, 1992, in the name of McCormack et al., the contents of which are incorporated herein.

The size of the outer cover 12 is typically determined by the size of the absorbent material 16 and the exact diaper design selected. Outer cover 12, for example, may be generally T-shaped, generally I-shaped, or may have a modified hourglass shape, and may extend beyond the terminal edges of the absorbent material 16 by a selected distance, such as a distance within the range of from about 1.3 centimeters to about 2.5 centimeters (about 0.5 to about 1.0 inch).

The body-side liner 14 and outer cover 12 are connected or otherwise associated together in an operable manner. As used herein, the term "associated" encompasses configurations in which the body-side liner 14 is directly joined to the outer cover 12 by affixing liner 14 directly to outer cover 12, and configurations wherein liner 14 is joined to outer cover 12 by affixing liner 14 to intermediate members which, in turn, are affixed to outer cover 12. The liner 14 and outer cover 12 can be affixed directly to each other in the diaper periphery 38 by attachment means (not shown) such as adhesive bonds, sonic bonds, thermal bonds, or any other attachment means known in the art. For example, a uniform continuous layer of adhesive, a patterned layer of adhesive, a sprayed pattern of adhesive or an array of separate lines, swirls, or spots of construction adhesive may be used to affix the body-side liner 14 to outer cover 12. The above-described attachment means may also be employed to interconnect and assembly together the other component parts of the absorbent article.

The ears 26 may be integrally formed with diaper 10, in which case the ears 26 are generally extensions of the outer cover 12 and/or body-side liner 14. Alternatively, the ears 26 can be separately formed and then attached to the diaper 10. FIG. 1 illustrates the embodiment wherein ears 26 are separately formed and then attached to the diaper 10. In the illustrated embodiment, ear 26 is attached to diaper 10 by sandwiching the ear between unadhered portions of the outer cover 12 and body-side liner 14 and then adhering the three materials (outer cover, body-side liner and ear) together by means such as adhesive bonding, thermal bonding, sonic bonding, and the like. The ears 26 can be made out of any material possessing the integrity which allows it to function as herein described. Suitably, the ear 26 may be formed out of a material such as that used to form the outer cover and/or body-side liner. Suitable materials from which the ear may be formed include films, nonwoven materials, woven or knit materials, foams, and composites and laminates of the above materials. The ear may be formed from an elastic material such as elastomeric films, e.g., natural or synthetic rubber; elastomeric strands, e.g., Lycra™ strands; elastomeric foams, e.g., urethane foams; elastomeric nonwoven materials; laminates or composites of such elastomeric materials with other elastomeric or non-elastomeric materials, e.g., neck-bonded laminates or stretch-bonded laminates; and the like. When the ear is formed from an elastic material, the elastic material can suitably be elongated to from about 75 percent to about 150 percent of its relaxed length, more specifically from about 100 percent to about 150 percent of its relaxed length. Elongations within these ranges are believed to result in the best fit in use.

A first mechanical fastener is attached to ear 26. The first mechanical fastener is adapted to releasably engage with a second mechanical fastener located in the rear portion of diaper 10. In the illustrated embodiment, the first mechanical fastener comprises hook members 34 of a hook-and-loop fastener which are adapted to engage with a loop material. The second mechanical fastener comprises loop members 36 of a hook-and-loop fastener attached to the outer surface of outer cover 12. The loop members comprise a plurality of loops adapted to releasably engage with the hooks present on the hook members. Other suitable mechanical fasteners are known to those skilled in the art and include adhesives, cohesives, buttons, snaps, clips, and the like.

In the embodiment illustrated in FIG. 1, the diaper 10 further comprises a pair of opposed ears 40 located on the rear portion of the diaper 10. The ears 40 located on the rear portion 20 can be formed and attached as described above in connection with ears 26.

Figure 2:
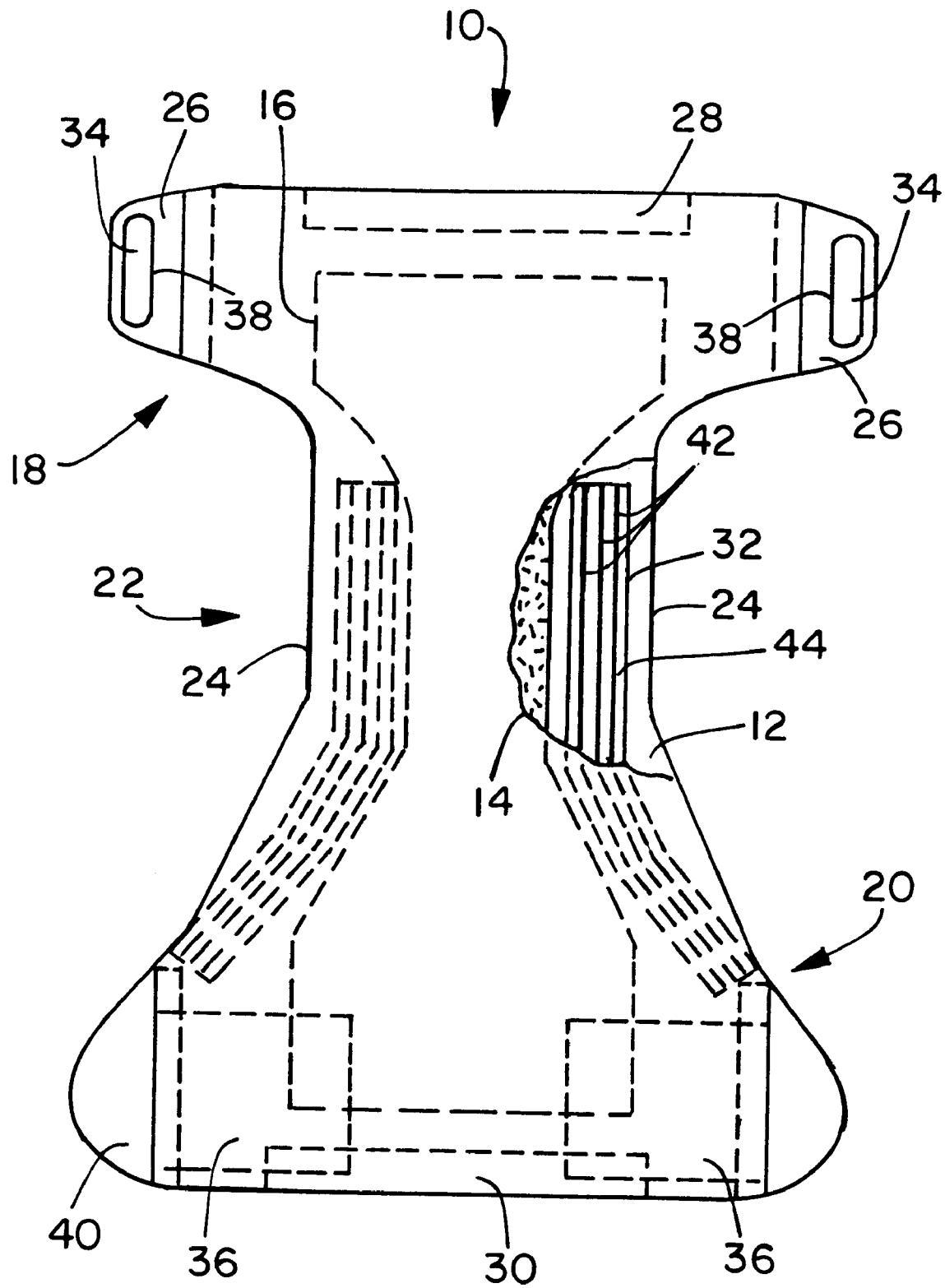
FIG. 2 is a plan view of a second embodiment of a disposable diaper according to the present invention.
Figure 3:
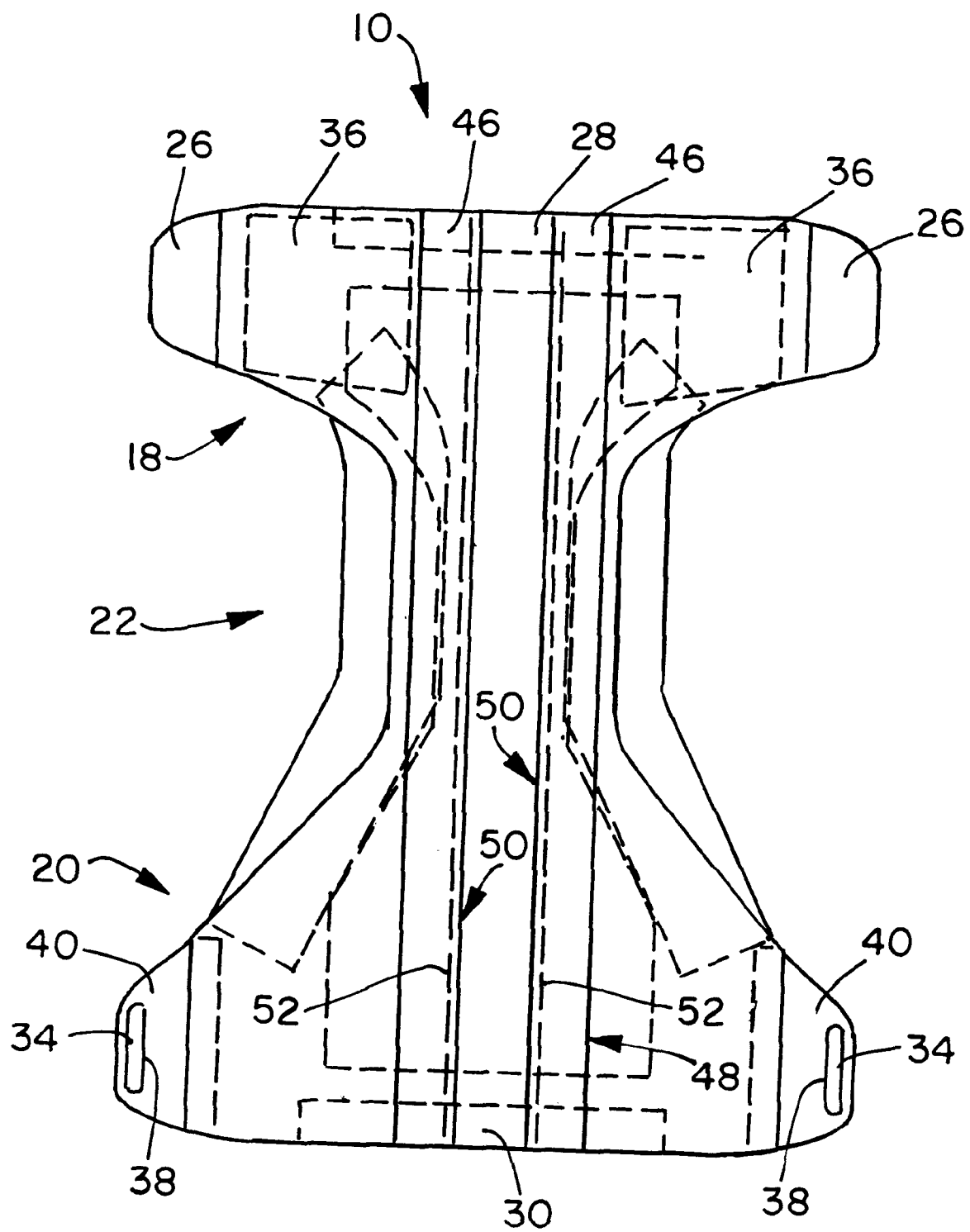
FIG. 3 is a plan view of a third embodiment of a disposable diaper according to the present invention.

In the embodiment illustrated in FIGS. 1–3, the hook members 34 are located in a generally oblong area having a length of up to about 3.5 inches (8.9 centimeters), specifically of about 2.75 inches (7.0 centimeters), and a width of about 0.5 inch (1.3 centimeters). The loop members 36 generally span an area between an upper edge 41 of the diaper 10 and the leg elastic members 32. The loop members 36 can be dimensioned to ensure proper attachment of the diaper about the waist of a wearer. Specifically, the loop members can have a dimension across the width of the diaper which will prevent forming attachment points other than on the side of the diaper and within the desired distance from the transverse center plane.

The loop material may generally have a width (dimension along the width of the article) of from about 2.5 inches (6.4 centimeters) to about 5.5 inches (14 centimeters), particularly of from about 3.0 inches (7.6 centimeters) to about 3.5 inches (8.9 centimeters), and a length of from about 2.0 inches (5.1 centimeters) to about 3.5 inches (8.9 centimeters), particularly of from about 2.5 inches (6.4 centimeters) to about 2.75 inches (7.0 centimeters).

Front waist elastic member 28 and rear waist elastic member 30 are suitably formed from any elastic material capable of extending at least about 10 percent and, preferably, at least about 100 percent of its relaxed length. The front and rear waist elastic members are secured to the diaper 10 in an elastically contractible condition so that, in a normal, unrestrained configuration, the elastic members effectively contract against diaper 10. The front and rear waist elastic members may be attached in at least two ways. For example, the elastic members may be stretched and secured to diaper 10 while diaper 10 is in an uncontracted condition. Alternatively, diaper 10 may be contracted, for example, by pleating, and the elastic member secured and connected to the diaper 10 while the elastic members are in an unstretched condition. Still other means, such as heat-shrink elastic material, may be used to form the front and rear waist elastic members. Exemplary of materials from which the front and rear waist elastic members can be formed are elastomeric films, e.g., natural or synthetic rubber; elastomeric strands, e.g., Lycra™ strands; elastomeric foams, e.g., urethane foams; elastomeric nonwoven materials; laminates or composites of such elastomeric materials with other elastomeric or non-elastomeric materials, e.g., neck-bonded laminates or stretch-bonded laminates; and the like.

In the embodiment illustrated in FIG. 1, leg elastic members 32 are separate elements attached to the inner surface of outer cover 12. That is, the leg elastic members 32 are attached between the outer cover 12 and the body-side liner 14. The leg elastic members 32 may, alternatively, be attached to the outer surface of the outer cover 12. A portion of leg elastic members 32 extends beyond the opposed longitudinal side edges 24 of the diaper 10. Any elastic material is believed suitable for use in forming the leg elastic members. Exemplary of such materials are elastomeric films, e.g., natural or synthetic rubber; elastomeric strands, e.g., Lycra® strands; elastomeric foams, e.g., urethane foams; elastomeric nonwoven materials; laminates or composites of such elastomeric materials with other elastomeric or non-elastomeric materials, e.g., neck-bonded laminates or stretch-bonded laminates; Lycra® strands attached to a nonwoven; and the like.

The leg elastic members 32 may be attached to the diaper 10 in either a stretched or unstretched condition. When the leg elastic members 32 comprise a material which is uniformly elastic, such as an elastomeric foam or a laminate of an elastomeric film or strands and a spunbond material, it is often preferred that the leg elastics be joined to the diaper in an unstretched condition.

In one preferred embodiment, the leg elastic members 32 are curved and extend from the front portion 18 through the crotch portion 22 and into rear portion 20. Specifically, the leg elastic members are curved outward (away from a central longitudinal axis of the article) from the crotch portion to the rear portion. For example, the leg elastic members may be curved outward into the rear portion to form an angle alpha (FIG. 1) of about 75 degrees or less, particularly of about 70 degrees or less, more particularly of about 60 degrees or less. Specifically, angle alpha may be defined by (1) a line, parallel to longitudinal center axis X and passing through a point of leg elastic members 32 closest to the longitudinal center axis X and (2) an edge of leg elastic member 32.

Moreover, the leg elastic members may extend into the rear portion a sufficient distance to cause the rear portion to become cup shaped. That is, to cause the ear portions 40 to curve upward and inward. Formation of the cup-shaped rear portion has been found to occur when the leg elastic members extend into an abutting or overlapping relationship pith the loop material 36 or ear 40, that is, when a portion of the leg elastic members 32 contacts, or is within about 1.0 inch (2.54 centimeters), particularly within about 0.5 inch (1.27 centimeters), of the loop material 36 or ear 40.

Formation of the cup-shaped rear portion has been found to allow for more efficient use of the diaper. Specifically, when the wearer is laid on the diaper, the cup-shaped rear portion has been found to conform to the shape of the wearer, thus, causing the ears 40 to partially encircle the waist of the wearer. This, in turn, causes the loop members 36 to become located on the sides of the wearer and, thus, exposed and available for engagement with the hook members 34. The care giver can then grasp an ear 26 in each hand, pull the front portion up and over the front of the wearer and simultaneously engage both hook members 34 with their respective loop member 36. Simultaneous attachment of both pairs of hook-and-loop members allows for achieving a proper fit the first time attachment of the hook-and-loop members is made. 1f the two pairs of hook-and-loop members are attached separately, it is often necessary to disengage and refasten the first-attached pair in order to obtain a correct fit.

The absorbent material 16 is adapted to absorb body exudates. Any material capable of performing such a function is believed suitable for use in the present invention. The absorbent material may comprise a single, integral piece of material or, alternatively, may comprise a plurality of individual separate pieces of material which are operably assembled together. The absorbent material 16 may be manufactured in a wide variety of sizes and shapes (for example, rectangular, trapezoidal, T-shaped, I-shaped, hourglass shaped, etc.), and from a wide variety of materials. The size and the absorbent capacity of the absorbent material 16 should be compatible with the size of the intended wearer and the liquid loading imparted by the intended use of the absorbent article. The size and the absorbent capacity of the absorbent material 16 can be varied to accommodate wearers ranging from infants through adults.

Various types of wettable, hydrophilic, fibrous material can be used to form the absorbent material 16. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of inherently wettable material, such as glass fibers; synthetic fibers made from inherently wettable thermoplastic polymers, such as particular polyester or polyamide fibers; and synthetic fibers composed of a non-wettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the non-wettable, hydrophobic fiber with a hydrophilic polymer during or after the formation of the fiber. For the purposes of the present invention, it is contemplated that selected blends of the various type of fibers mentioned above may also be employed.

As used herein, the term "hydrophilic" describes fibers, or the surfaces of fibers, which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 surface force analyzer system. When measured with this system, fibers having contact angles less than 90 degrees are designated "wettable", while fibers having contact angles greater than 90 degrees are designated "non-wettable."

In addition to the fibrous material described above, the absorbent material 16 may further comprise a high-absorbency material such as those known in the art as "superabsorbents." High-absorbency materials can be natural, synthetic, and modified natural polymers and materials. In addition, the high-absorbency materials can be inorganic materials such as silica gels, or organic compounds such as crosslinked polymers. The term "crosslinked" refers to any means for effectively rendering normal water-soluble materials substantially water insoluble but swellable. Such means can include, for example, physical entanglement, crystalline domains, covalent bonds, ionic complexes and associations, hydrophilic associations such as hydrogen bonding, and hydrophobic associations or van der Waals forces.

Examples of synthetic high-absorbency materials include polymeric materials such as alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol) and mixtures and copolymers thereof. Further polymers suitable for use in the absorbent material include natural and modified natural polymers, such as hydrolyzed acrylonitrile-grafted starch, acrylic acid-grafted starch, methyl cellulose, carboxymethyl cellulose, hydroxypropyl cellulose, carboxymethyl starch, and the natural gums, such as alginates, xanthan gum, locust bean gum, and the like. Mixtures of natural and wholly, or partially, synthetic absorbent polymer can also be useful in the present invention. Other suitable high-absorbency materials are disclosed by Assarson et al. in U.S. Pat. No. 3,902,236 issued Aug. 26, 1975. Processes for preparing synthetic, high-absorbency materials are disclosed in U.S. Pat. No. 4,076,663 issued Feb. 28, 1978, to Masuda et al. and U.S. Pat. No. 4,286,082 issued Aug. 25, 1981, to Tsubakimoto et al.

FIG. 2 illustrates an alternative embodiment according to the present invention. The diaper 10 illustrated in FIG. 2 comprises leg elastic members 32 which comprise elastomeric strands 42 which are attached to the diaper 10 between outer cover 12 and body-side liner 14 in the diaper periphery 38. The elastomeric strands 42 are located in the crotch portion 22 of the diaper 10 adjacent the opposed longitudinal side edges 24. The elastic strands 42 may have any of a multitude of configurations. For example, the width of the individual elastic strands 42 may be varied from 0.25 millimeter (0.01 inches) to 25 millimeters (1.0 inch) or more. The elastic strands may comprise a single strand of elastic material, or may comprise several parallel or non-parallel strands of elastic material, or may be applied in a rectilinear or curvilinear arrangement. The elastic strands may be affixed to the diaper in any of several ways which are known in the art. For example, the elastic strands may be ultrasonically bonded, heat and pressure sealed using a variety of bonding patterns, or adhesively bonded to diaper 10 with sprayed or swirled patterns of hot-melt adhesive.

In the embodiment illustrated in FIG. 2, leg elastic members 32 may comprise a carrier sheet 44 to which elastic strands 42 are attached. The carrier sheet may, for example, comprise a 0.002 centimeter thick film of unembossed polypropylene material. The illustrated elastic strands can, for example, be composed of Lycra™ elastomer available from DuPont (Wilmington, Del.). Each elastic strand is typically from within the range of about 620–1,050 decitex and, preferably, is about 940 decitex in an embodiment of the invention wherein 3 strands are employed for each leg elastic member.

As discussed above, leg elastic members 32 may be generally straight but are desirably curved. For example, the leg elastics illustrated in FIG. 2 can be inwardly bowed toward the longitudinal center axis of the diaper with the innermost point (or apex relative to the cross direction of the article) of the set of curved elastic strands positioned approximately 0.75–2.0 inches inward from the outermost edge of the set of elastic strands.

FIG. 3 illustrates still a further embodiment of the present invention. As can be seen from reference to FIG. 3, hook members 34 can, alternatively, be located on rear ear 40, while loop members 36 are located on the outer surface of the front portion 18 of diaper 10. In such a situation, rather than having the front-to-back fastening illustrated on the diapers of FIGS. 1 and 2, FIG. 3 illustrates a diaper having a more traditional back-to-front fastening. Nonetheless, the opposed ears 40 located on the rear portion are adapted, in use, to overlap with the front portion of the article. The hook-and-loop members, for attaching the overlap portion of the ears 40 to the front portion 18, form attachment points. The attachment points are located on the side of the diaper behind a transverse center plane of the diaper.

FIG. 3 further comprises containment flaps 46 including proximal edges 48 and distal edges 50. The containment flaps 46 may be formed in a wide variety of configurations known to those skilled in the art. Suitably, proximal edges 48 are attached to, or integrally formed from, the body-side liner 14. The distal edges 50 are generally unattached to the body-side liner 14 at least in the crotch portion 22. In this manner, the containment flaps serve to form a barrier to the lateral flow of body exudates. The containment flaps may further comprise containment flap elastics 52 which serve to maintain the containment flaps 46 in a generally upright configuration. Those skilled in the art will recognize that containment flaps 46 may be separate, add-on flaps or may be integrally formed from the body-side liner 14.

Diaper configurations suitable for use in the present invention are explained in greater detail in the following U.S. patents and patent applications, the disclosures of which are incorporated herein to the extent consistent herewith. U.S. patent application Ser. No. 07/757,760 filed Sep. 11, 1991, in the name of Hanson et al.; U.S. Pat. No. 4,149,335 issued Sep. 22, 1992, to Kellenberger et al.; U.S. Pat. No. 4,798,603 issued Jan. 17, 1989, to Meyer et al.; U.S. Pat. No. 4,704,116 issued Nov. 3, 1987, to Enloe; U.S. Pat. No. 5,147,343 issued Sep. 15, 1992, to Kellenberger; and U.S. patent application Ser. No. 07/997,800, filed Dec. 29,1992, in the name of McCormack et al. previously incorporated herein by reference.

As generally discussed above, the absorbent article of the present invention comprises attachment means for attaching an overlapped portion of ears located on the front or rear portion of the diaper to a respective rear or front portion of the diaper. This attachment forms attachment points which are located on the side of the diaper behind a transverse center plane of the diaper. As used herein, a transverse center plane of an article, such as a diaper, is intended to refer to a plane which transversely bisects the absorbent article through the crotch portion when the attachment means are attached to form attachment points and, therefore, a three-dimensional article. Specifically, a longitudinal central axis of the article is determined (line X in FIG. 1). A transverse central axis perpendicular to the longitudinal central axis is determined (line Y in FIG. 1). The attachment means are attached to form attachment points and a three-dimensional article. A longitudinal center plane passes through and contains the longitudinal central axis. The transverse center plane described herein is perpendicular in all aspects to the longitudinal central plane and passes through and contains the transverse center axis.

Figure 5:
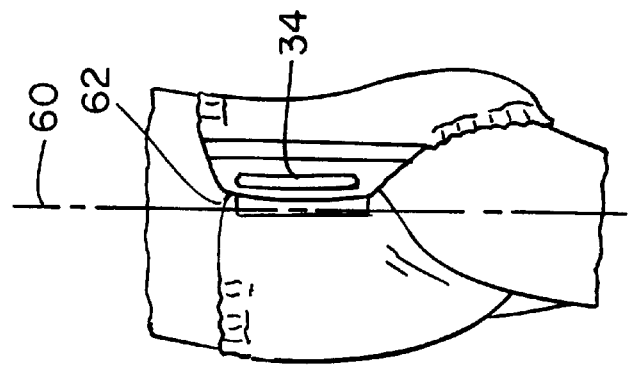
FIG. 5 illustrates a side view of the disposable diaper illustrated in FIG. 3 in use on an infant.
Figure 4C:
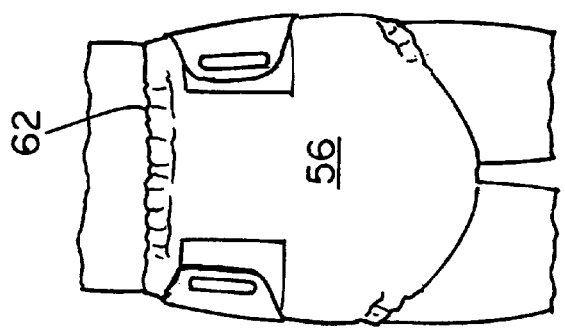
FIGS. 4A–4C illustrate the disposable diaper illustrated in FIG. 1 in use on an infant.
Figure 4B:
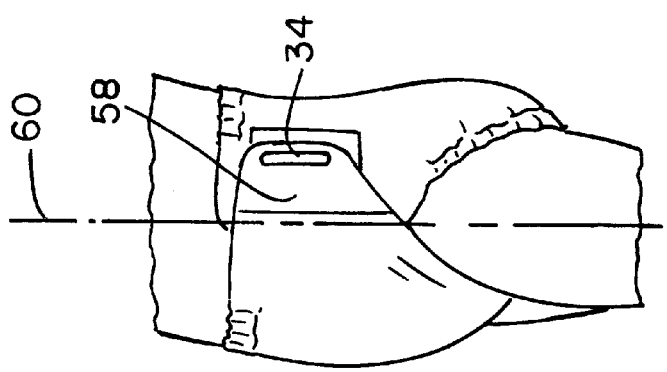
Figure 4A:
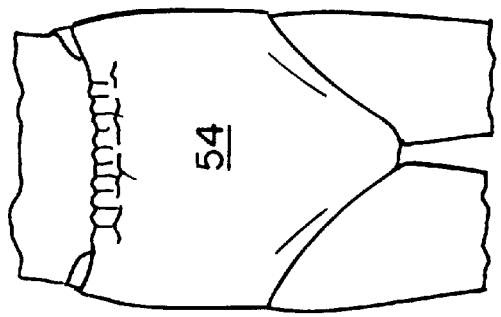

This aspect of the invention can best be understood by reference to FIGS. 4 and 5. FIG. 4 illustrates the absorbent article illustrated in FIG. 1 in place on a wearer. As can be seen from reference to FIG. 4, when the attachment means are attached to form attachment points, that is, when the hook-and-loop members are engaged, a three-dimensional article is defined. The article comprises a front panel 54, a rear panel 56, and sides 58. A transverse center plane 60 is illustrated in FIGS. 4 and 5. The transverse center plane 60 transversely bisects the article when the attachment means are engaged.

The transverse center plane of the article will, in the preferred embodiment, coincide or nearly coincide with the transverse center plane of the wearer. The transverse center plane of a wearer is that plane which is perpendicular to a plane on which the wearer is standing and passes through the center of both ankles and both ear lobes of the wearer when the wearer is standing upright with feet together.

The front and rear portions of the article, as well as the ears present on the article, are configured so that there is overlap between the front portion and rear portion of the article at sides 58. In the overlapping area defined by the front and rear portions, the attachment means, for example, hook-and-loop members, are attached to form attachment points. Applicants have found that by having at least some, preferably all, of the attachment points located on the side of the article behind a transverse center plane of the article, improved fit and less drooping in the front panel 54 of the article is achieved. As used herein, reference to an area "behind the transverse center plane" is intended to refer to that area which is closer to back panel 56 than to front panel 54 when moving along the outer circumference of the diaper 10. Thus, in both FIGS. 4 and 5, hook members 34 are located "behind the transverse center plane" 60. Moreover, Applicants have found that particularly improved fit is obtained when at least some, desirably a majority, and preferably all, of the attachment points are located within 2.5 inches (6.4 centimeters), beneficially within about 1.5 inches (3.8 centimeters) and preferably within about 1.0 inch (2.5 centimeters) of said transverse center plane. By having the attachment points be located within about 1.0 inch of the transverse center plane, it can be assured that the attachment points are located at the sides of the article 10. In one specific embodiment, at least some of the attachment points are located within about 0.1 inch (0.254 centimeter) of the transverse center plane.

The improved fit obtained by the described positioning of the attachment points is believed to result, at least in part, from the fact that the described positioning results in the attachment points being located on a portion of a wearer which does not flex with movement of the wearer. Specifically, the attachment points are generally located over the hip bones of a wearer, thus, subjecting the attachment points to less movement (sheer forces) during movement of the wearer. Further, the force vector created by the attachment illustrated in FIG. 4 is upward and toward the rear of the wearer. This serves to prevent or reduce drooping in the front panel of the diaper.

FIG. 4 illustrates a front-to-back fastening wherein the front portion overlaps the rear portion to engage the attachment means. FIG. 5 illustrates a back-to-front fastening therein the back portion overlaps the front portion to allow for engagement of the attachment means.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disposable absorbent article, said article defining a front portion, a rear portion and a crotch portion connecting the front and rear portions and having opposed longitudinal side edges, said article comprising:

an outer cover;

a liquid-pervious body-side liner;

an absorbent material located between said outer cover and said body-side liner;

a pair of opposed ears located on said front portion, said ears being adapted, in use, to overlap with said rear portion of said article to form overlapped portions;

attachment means for attaching said overlapped portions of said ears to said rear portion to form attachment points, said attachment points being located on a side of said article behind a transverse center plane of said article and within about 2.5 inches (6.4 centimeters) of said transverse center plane;

a waist elastic member attached to at least one of said front portion or said rear portion; and leg elastic members attached to said crotch portion adjacent said opposed longitudinal side edges.

2. The absorbent article according to claim 1 wherein said ears are non-integrally formed with said front portion.

3. The absorbent article according to claim 1 wherein said attachment means comprise a first mechanical fastener attached to said ears and adapted to releasably engage with a second mechanical fastener attached to said rear portion.

4. The absorbent article according to claim 3 wherein said first mechanical fasteners are hook members of a hook-and-loop fastener and said second mechanical fasteners are loop members of a hook-and-loop fastener.

5. The absorbent article according to claim 3 wherein said first mechanical fastener has a length of up to about 3.5 inches (8.9 centimeters).

6. The absorbent article according to claim 1 wherein all of said attachment points are located within about 1.5 inches (3.8 centimeters) of said transverse center plane.

7. The absorbent article according to claim 6 wherein all of said attachment points are located within about 1.0 inch (2.54 centimeters) of said transverse center plane.

8. The absorbent article according to claim 1 wherein said waist elastic member is attached to said front portion and said absorbent article further comprises a waist elastic member attached to said rear portion.

9. The absorbent article according to claim 1 wherein said leg elastic members are separate elements which extend beyond said opposed longitudinal side edges.

10. The absorbent article according to claim 1 wherein said leg elastic members are located between said body-side liner and said outer cover.

11. The absorbent article according to claim 1 wherein said leg elastic members curve outward into the rear portion at an angle of about 75 degrees or less.

12. The absorbent article according to claim 11 wherein said leg elastic members curve outward into the rear portion at an angle of about 60 degrees or less.

13. The absorbent article according to claim 1 wherein said leg elastic members cause the rear portion to become cup shaped.

14. The absorbent article according to claim 4 wherein said leg elastic members abut or overlap with said loop members.

15. A disposable absorbent article, said article defining a front portion, a rear portion, and a crotch portion connecting the front and rear portions and having opposed longitudinal side edges, said article comprising:

an outer cover;

a liquid-pervious body-side liner;

an absorbent material located between said outer cover and said body-side liner;

a pair of opposed ears located on said rear portion, said ears being adapted, in use, to overlap with said front portion of said article to form an overlapped portion;

attachment means for attaching said overlapped portion of said ears to said front portion to form attachment points, said attachment points being located on a side of the article behind a transverse center plane of said article and within about 2.5 inches (6.4 centimeters) of said transverse center plane;

a waist elastic member attached to at least one of said front or rear portion; and leg elastic members attached to said crotch portion adjacent said opposed longitudinal side edges.

16. The absorbent article according to claim 15 wherein said ears are non-integrally formed with said rear portion.

17. The absorbent article according to claim 15 wherein said attachment means comprise a first mechanical fastener attached to said ears and adapted to releasably engage with a second mechanical fastener attached to said front portion.

18. The absorbent article according to claim 17 wherein said first mechanical fasteners are hook members of a hook-and-loop fastener and said second mechanical fasteners are loop members of a hook-and-loop fastener.

19. The absorbent article according to claim 18 wherein said first mechanical fastener has a length of up to 3.5 inches (8.9 centimeters).

20. The absorbent article according to claim 15 wherein all of said attachment points are located within about 1.5 inches (3.8 centimeters) of said transverse center plane.

21. The absorbent article according to claim 20 wherein all of said attachment points are located within about 1.0 inches (2.54 centimeters) of said transverse center plane.

22. The absorbent article according to claim 15 wherein said waist elastic member is attached to said front portion and said absorbent article further comprises a waist elastic member attached to said rear portion.

23. The absorbent article according to claim 15 wherein said leg elastic members are separate elements which extend beyond said opposed longitudinal side edges.

24. The absorbent article according to claim 15 wherein said leg elastic members are located between said body-side liner and said outer cover.

25. A disposable absorbent article, said article defining a front portion, a rear portion, and a crotch portion connecting the front and rear portions and having opposed longitudinal side edges, said article comprising:

an outer cover;

a liquid-pervious body-side liner;

an absorbent material located between said outer cover and said body-side liner;

a pair of opposed ears located on said front portion, said ears being adapted, in use, to overlap with said rear portion of said article;

a first mechanical fastener attached to said opposed ears;

a second mechanical fastener attached to said outer cover in said rear portion and being configured to releasably engage with said first mechanical fastener to define attachment points; all of said attachment points being located behind a transverse center plane of said article and within about 2.5 inches (6.4 centimeters) of said transverse center plane; and leg elastic members attached to said crotch portion adjacent said opposed longitudinal side edges.

26. The absorbent article according to claim 25 wherein said first mechanical fasteners are hook members of a hook-and-loop fastener and said second mechanical fasteners are loop members of a hook-and-loop fastener.

27. The absorbent article according to claim 26 wherein said leg elastic members abut or overlap with said loop members.

28. The absorbent article according to claim 25 wherein said leg elastic members curve outward into the rear portion at an angle of about 75 degrees or less.

29. The absorbent article according to claim 28 wherein said leg elastic members curve outward into the rear portion at an angle of about 70 degrees or less.

30. The absorbent article according to claim 25 wherein said leg elastic members cause the rear portion to become cup shaped.

31. The absorbent article according to claim 25 further comprising a waist elastic member attached to at least one of said front or said rear portions.

* * * * *

(12) EX PARTE REEXAMINATION CERTIFICATE (6731st)
United States Patent
Suprise et al.

(10) Number: US 5,899,896 C1
(45) Certificate Issued: Mar. 31, 2009

(54) ABSORBENT ARTICLE WITH FASTENING SYSTEM TO PREVENT DROOPING

(75) Inventors: Jody Dorothy Suprise, Neenah, WI (US); Georgia Lynn Zehner, Larsen, WI (US); Paulette Mary Rosch, Sherwood, WI (US)

(73) Assignee: Kimberly-Clark Corporation, Neenah, WI (US)

Reexamination Request:
No. 90/007,304, Nov. 17, 2004

Reexamination Certificate for:
Patent No.: 5,899,896
Issued: May 4, 1999
Appl. No.: 08/148,101
Filed: Nov. 2, 1993

(51) Int. Cl.
*A61F 13/15* (2006.01)

(52) U.S. Cl. .................................. 604/391; 604/358
(58) Field of Classification Search .................. 604/358, 604/385.01, 385.201, 386, 387, 390–391, 604/393, 400
See application file for complete search history.

(56) References Cited

U.S. PATENT DOCUMENTS

| | | |
|---|---|---|
| 3,559,648 A | 2/1971 | Mason, Jr. |
| 3,860,003 A | 1/1975 | Buell |
| 4,014,340 A | 3/1977 | Cheslow |
| 4,205,679 A | 6/1980 | Repke et al. |
| 4,610,680 A | 9/1986 | LaFleur |
| 4,615,695 A | 10/1986 | Cooper |
| 4,699,622 A | 10/1987 | Toussant et al. |
| 4,753,650 A | 6/1988 | Williams |
| 4,850,992 A | 7/1989 | Amaral et al. |
| 4,895,568 A | 1/1990 | Enloe |
| 4,938,754 A | 7/1990 | Mesek |
| 4,978,345 A | * 12/1990 | Holliday et al. ............. 604/384 |
| 4,985,025 A | 1/1991 | Lingertat et al. |
| 5,055,103 A | 10/1991 | Nomura et al. |
| 5,062,839 A | 11/1991 | Anderson |
| 5,151,092 A | 9/1992 | Buell et al. |
| 5,176,671 A | 1/1993 | Roessler et al. |
| 5,269,776 A | 12/1993 | Lancaster et al. |
| 5,509,915 A | 4/1996 | Hanson et al. |
| 5,545,159 A | 8/1996 | Lancaster et al. |

FOREIGN PATENT DOCUMENTS

| | | |
|---|---|---|
| EP | 0 388 681 A2 | 9/1990 |
| EP | 0 528 282 A2 | 2/1993 |
| EP | 0 532 034 B2 | 3/1993 |
| EP | 0 604 731 A1 | 10/1993 |
| JP | H1-92403 | 4/1989 |

* cited by examiner

*Primary Examiner*—Jimmy G Foster

(57) ABSTRACT

The present invention is directed to an absorbent article which is configured to prevent drooping and to improve fit. The article comprises attachment means for attaching the article about the waist of a wearer such that attachment points are located on the sides of the article and behind a transverse center plane of the article.

At the time of issuance and publication of this cetificate, the patent remains subject to pending reissue application number 11/634,309 filed Dec. 5, 2006. The claim content of the patent may be subsequently revised in the reissue proceeding.

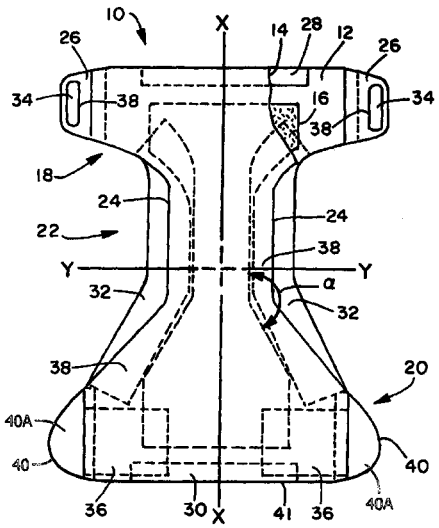

(AMENDED)

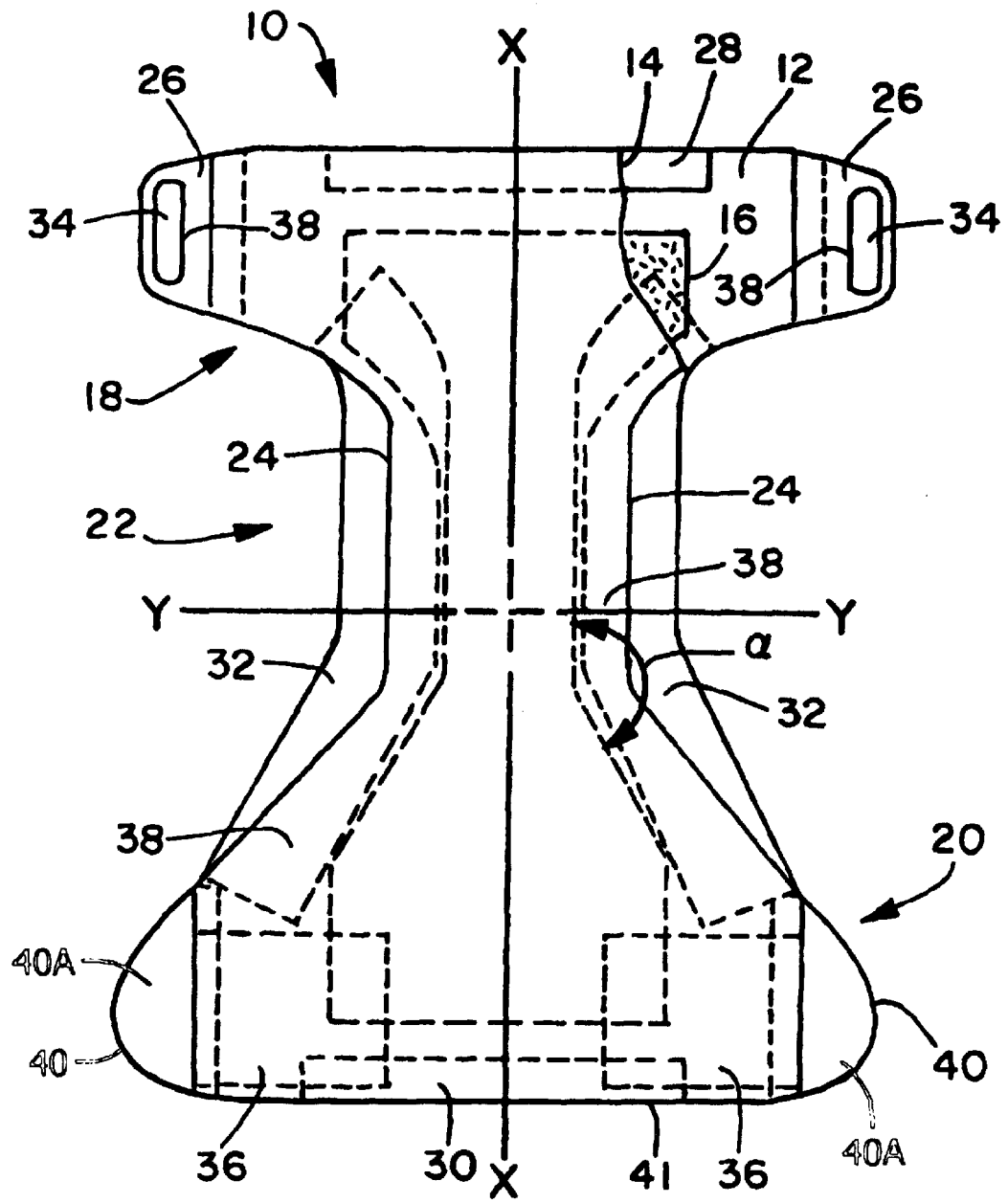
FIG. 1
(AMENDED)

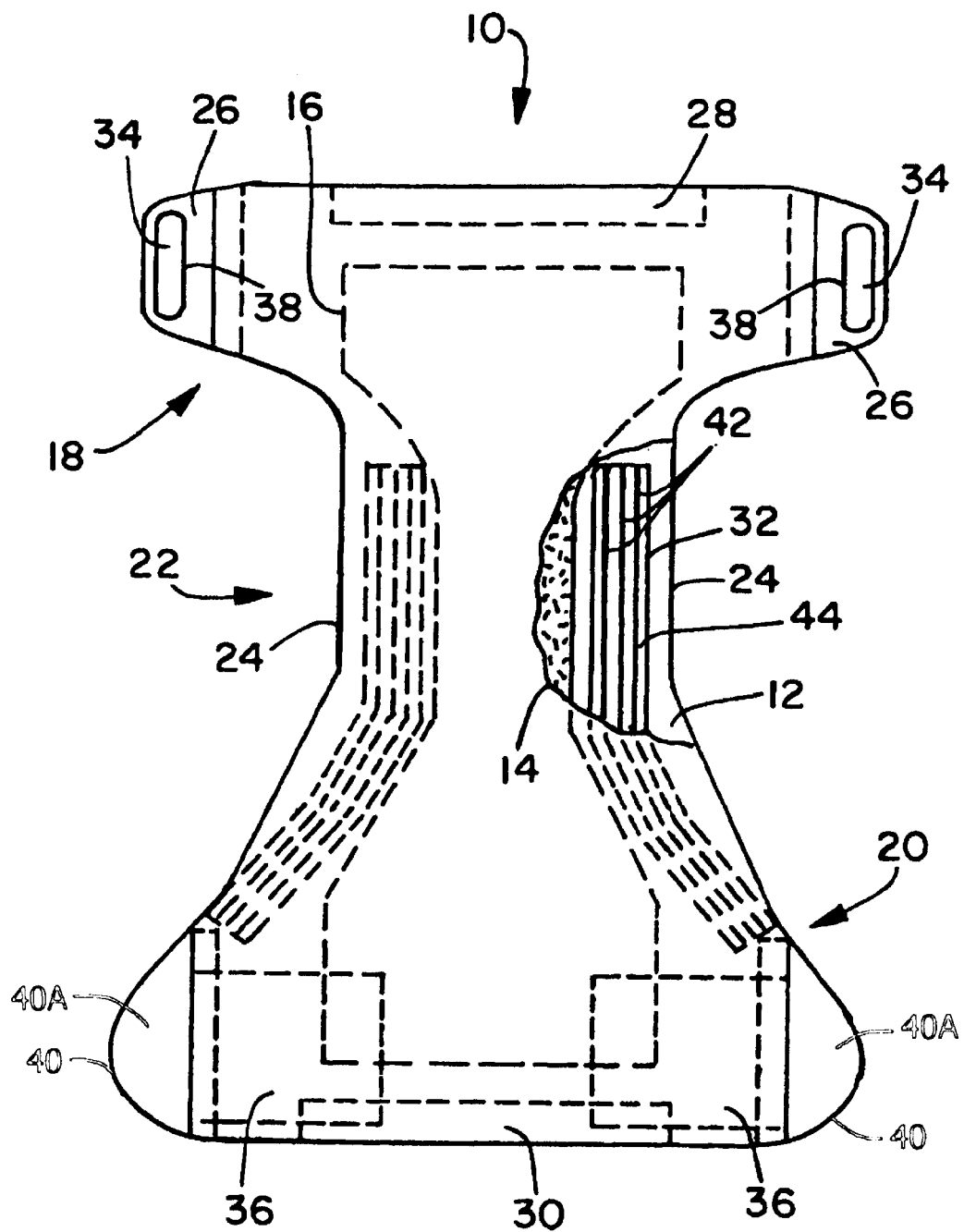
FIG. 2
(AMENDED)

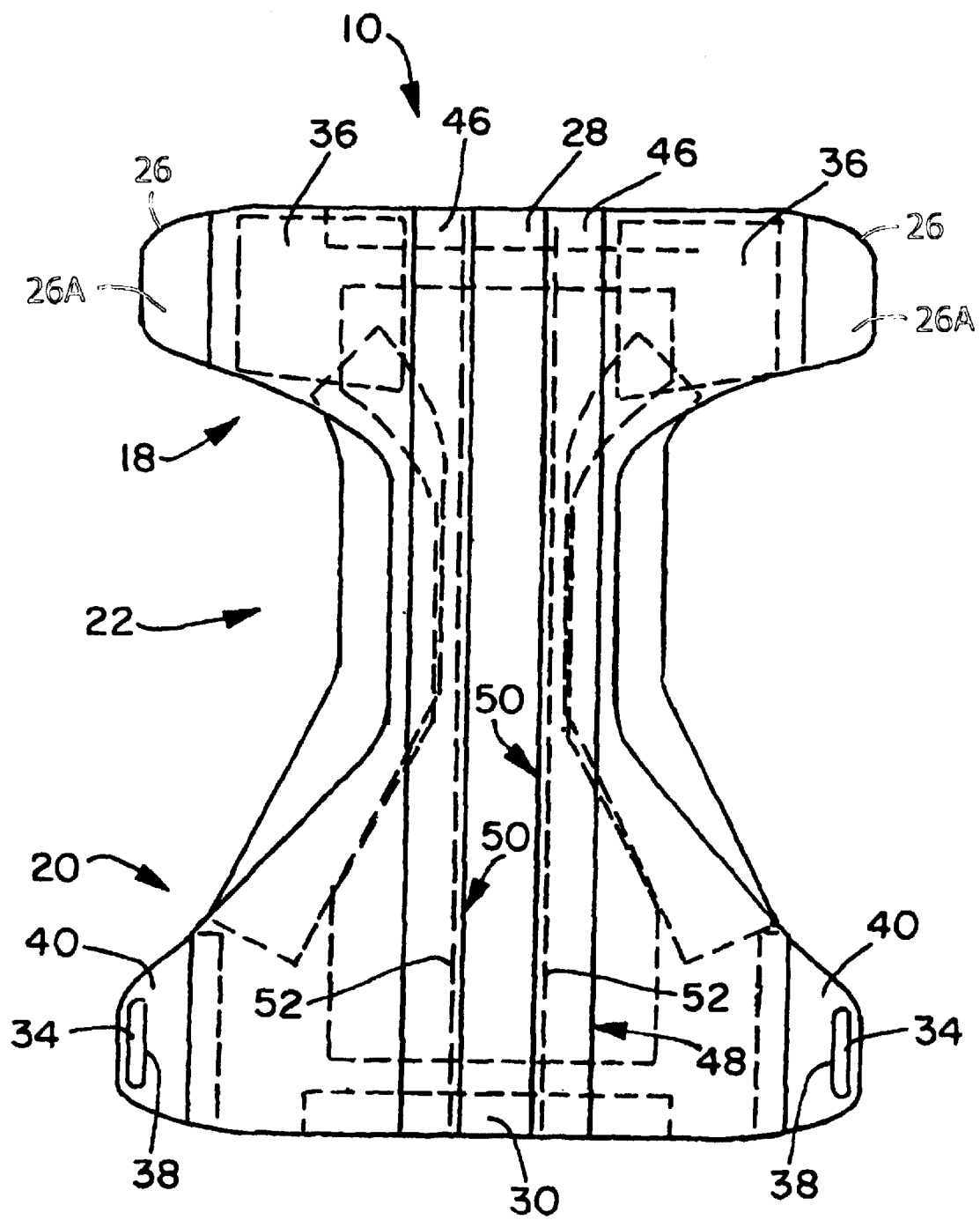
FIG. 3
(AMENDED)

US$5,899,896$ C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, line 10:

*In another embodiment, the present invention is directed to a disposable absorbent article defining a front portion, a rear portion and a crotch portion connecting the front and rear portions and having opposed longitudinal side edges. The article comprises an outer cover, a liquid-pervious body-side liner, and an absorbent material located between the outer cover and the body-side liner. A pair of opposed front ears is located on the front portion of the article. The front ears are adapted, in use, to overlap with the rear portion of the article to form overlapped portions, but not to overlap one another. Attachment means is provided for attaching the overlapped portions of the front ears to the rear portion to form attachment points for attachment of the article about the waist of a wearer without the use of other means. The attachment points are located on a side of the article behind a transverse center plane of the article and within about 2.5 inches (6.4 centimeters) of the transverse center plane. The attachment means is configured to prevent formation of any attachment points other than behind the transverse center plane. A pair of rear ears is located on the rear portion. The rear ears have outer fastener-free regions disposed laterally outward of the absorbent material and the leg elastic members. The fastener-free regions are adapted, in use, to extend forward past the transverse center plane and to be overlapped by the front portion of the article. A waist elastic member is attached to at least one of the front portion or the rear portion of the article. Leg elastic members are attached to the crotch portion adjacent the opposed longitudinal side edges. In some embodiments of this article, the attachment means comprises hook members on the ears and loop members on the rear portion. The hook and loop members are adapted to releasably engage to attach the article to the wearer without the use of other fasteners, and the loop members are dimensioned across a width of the article to prevent formation of attachment points other than behind the transverse center plane of the article. In some embodiments, the attachment means comprises a first mechanical fastener attached to each front ear on the front portion. The first mechanical fastener is oblong in the direction of a longitudinal central axis of the article.*

*In another embodiment, a disposable absorbent article of the present invention defines a front portion, a rear portion and a crotch portion connecting the front and rear portions and having opposed longitudinal side edges. The article comprises an outer cover, a liquid-pervious body-side liner, and an absorbent material located between the outer cover and the body-side liner. A pair of opposed ears is located on the front portion, the ears being adapted, in use, to overlap with the rear portion of the article to form overlapped portions. Attachment means is provided for attaching the overlapped portions of the ears to the rear portion to form attachment points. The attachment points are located on a side of the article behind a transverse center plane of the article and within about 2.5 inches (6.4 centimeters) of the transverse center plane. A waist elastic member is attached to at least one of the front portion or the rear portion. Leg elastic members are attached to the crotch portion adjacent the opposed longitudinal side edges. The leg elastic members cause the rear portion to become cup shaped. A pair of opposed rear ears is located on said rear portion of the article. The rear ears have outer fastener-free regions disposed laterally outward of the absorbent material and the leg elastic members. The fastener-free regions are adapted, in use, to extend forward past the transverse center plane and to be overlapped by the front portion of the article.*

*In another embodiment, a disposable absorbent article of the present invention defines a front portion, a rear portion, and a crotch portion connecting the front and rear portions and having opposed longitudinal side edges. The article comprises an outer cover, a liquid-pervious body-side liner, and an absorbent material located between the outer cover and the body-side liner. A pair of opposed ears is located on the rear portion, the rear ears being adapted, in use, to overlap with the front portion of the article to form an overlapped portion, but not to overlap one another. Attachment means is provided for attaching the overlapped portion of the rear ears to the front portion to form attachment points for attachment of the article about the waist of a wearer without the use of other means. The attachment points are located on a side of the article behind a transverse center plane of the article and within about 2.5 inches (6.4 centimeters) of the transverse center plane. The attachment means is configured to prevent formation of any attachment points other than behind the transverse center plane. A waist elastic member is attached to at least one of the front or rear portion. Leg elastic members are attached to the crotch portion adjacent the opposed longitudinal side edges. A pair of front ears is located on the front portion. The front ears have outer fastener-free regions disposed laterally outward of the absorbent material and the leg elastic members. The fastener-free regions are adapted, in use, to extend rearward past the transverse center plane and to be overlapped by the rear portion of the article. In some embodiments of this article, the attachment means comprises hook members on the ears and loop members on the front portion, the hook and loop members being adapted to releasably engage to attach the article to a wearer without the use of other fasteners. The loop members are dimensioned across a width of the article to prevent the formation of attachment points other than behind the transverse center plane of the article. In one embodiment, the attachment means comprises a first mechanical fastener attached to each rear ear on the rear portion of the article. The first mechanical fastener is oblong in the direction of a longitudinal central axis of the article.*

*In another embodiment, a disposable absorbent article of the present invention defines a front portion, a rear portion, and a crotch portion connecting the front and rear portions and having opposed longitudinal side edges. The article comprises an outer cover, a liquid-pervious body-side liner, and an absorbent material located between the outer cover and the body-side liner. A pair of opposed front ears is located on the front portion, the front ears being adapted, in use, to overlap with the rear portion of the article, but not to overlap one another. First mechanical fasteners are attached to the opposed ears. Second mechanical fasteners are attached to the outer cover in the rear portion and are con-* figured to releasably engage with respective first mechanical fasteners to define attachment points for attachment of the article about the waist of a wearer without the use of other means. All of the attachment points are located behind a transverse center plane of the article and within about 2.5 inches (6.4 centimeters) of the transverse center plane. The first and second mechanical fasteners are configured to prevent formation of any attachment points other than behind the transverse center plane. Leg elastic members are attached to the crotch portion adjacent the opposed longitudinal side edges. A pair of rear ears is located on the rear portion. The rear ears have outer fastener-free regions disposed laterally outward of the absorbent material and the leg elastic members. The fastener-free regions are adapted, in use, to extend forward past said transverse center plane and to be overlapped by the front portion of the article. In some embodiments, the each of the first mechanical fasteners is oblong in the direction of a longitudinal central axis of the article.

In another embodiment, a disposable absorbent article of the present invention defines a front portion, a rear portion, and a crotch portion connecting the front and rear portions and having opposed longitudinal side edges. The article comprises an outer cover, a liquid-pervious body-side liner, and an absorbent material located between the outer cover and the body-side liner. A pair of opposed front ears is located on the front portion, the front ears being adapted, in use, to overlap with the rear portion of the article. First mechanical fasteners are attached to the opposed ears. Second mechanical fasteners are attached to the outer cover in the rear portion and are configured to releasably engage with the first mechanical fastener to define attachment points. All of the attachment points are located behind a transverse center plane of the article and within about 2.5 inches (6.4 centimeters) of the transverse center plane. The leg elastic members are attached to the crotch portion adjacent the opposed longitudinal side edges. The leg elastic members cause the rear portion to become cup shaped. A pair of opposed rear ears is located on the rear portion of the article. The rear ears have outer fastener-free regions disposed laterally outward of the absorbent material and the leg elastic members. The fastener-free regions are adapted, in use, to extend forward past said transverse center plane and to be overlapped by the front portion. In some embodiments of this article, a rear waist elastic member is attached to the rear portion of the article. The leg elastic members terminate short of the rear waist elastic member, and the leg elastic members curve laterally outward beyond the absorbent member.

In another embodiment, a disposable absorbent article of the present invention defines a front portion, a rear portion and a crotch portion connecting the front and rear portions and having opposed longitudinal side edges. The article comprises an outer cover, a liquid-pervious body-side liner, an absorbent material located between the outer cover and the body-side liner, and a pair of opposed ears located on the front portion, the ears being adapted, in use, to overlap with the rear portion of the article to form overlapped portions, but not to overlap one another. Attachment means is provided for attaching the overlapped portions of the ears to the rear portion to form attachment points, the attachment points being located on a side of the article behind a transverse center plane of the article and within about 2.5 inches (6.4 centimeters) of the transverse center plane. A waist elastic member is attached to at least one of the front portion or the rear portion. Leg elastic members are attached to the crotch portion adjacent the opposed longitudinal side edges. The attachment means is constituted solely by first mechanical fasteners on a body side of the ears and second mechanical fasteners on the outer cover. The first mechanical fasteners are hook members of hook and loop fasteners and the second mechanical fasteners are loop members of hook and loop fasteners. The hook members are adapted to releasably engage respective loop members to hold the ears overlapped with the rear portion on the outside of the rear portion. The article lacks any means other than the hook members of the first mechanical fasteners and the loop members of the second mechanical fasteners for holding the overlapped portions of the article in position. The first and second mechanical fasteners are configured such that when the article is laid flat on a surface, all of the hook members of each first mechanical fastener are positioned laterally outward beyond all of the loop members of a respective second mechanical fastener. A pair of rear ears is located on the rear portion. The rear ears have outer fastener-free regions disposed laterally outward of the absorbent material and the leg elastic members. The fastener-free regions are adapted, in use, to extend forward past the transverse center plane and to be overlapped by the front portion of the article. In some embodiments of this article, the first mechanical fasteners do not extend laterally outward beyond the ears on the front portion. In some embodiments of this article, the second mechanical fasteners are dimensioned across a width of the article to prevent the formation of attachment points other than behind the transverse center plane of the article.

In another embodiment, a disposable absorbent article of the present invention defines a front portion, a rear portion and a crotch portion connecting the front and rear portions and having opposed longitudinal side edges. The article comprises an outer cover, a liquid-pervious body-side liner, and an absorbent material located between the outer cover and the body-side liner. A pair of opposed ears is located on the front portion, the ears being adapted, in use, to overlap with the rear portion of the article to form overlapped portions, but not to overlap one another. Attachment means is provided for attaching the overlapped portions of the ears to the rear portion to form attachment points. The attachment points are located on a side of the article behind a transverse center plane of the article and within about 2.5 inches (6.4 centimeters) of the transverse center plane. A waist elastic member is attached to at least one of the front portion or the rear portion. Leg elastic members are attached to the crotch portion adjacent the opposed longitudinal side edges. The attachment means is constituted solely by first mechanical fasteners on a body side of the ears and second mechanical fasteners on the outer cover. The first mechanical fasteners are hook members of hook and loop fasteners and the second mechanical fasteners are loop members of hook and loop fasteners. The hook members are adapted to releasably engage respective loop members to hold the ears overlapped with the rear portion on the outside of the rear portion. The article lacks any means other than the hook members of the first mechanical fasteners and the loop members of the second mechanical fasteners for holding the overlapped portions of the article in position. The first and second mechanical fasteners are configured such that when the article is laid flat on a surface, the hook members of each first mechanical fastener do not extend laterally outward beyond a respective ear. A pair of rear ears is located on the rear portion. The rear ears have outer fastener-free regions disposed laterally outward of the absorbent material and the leg elastic members. The fastener-free regions are adapted, in use, to extend forward past the transverse center plane and to be overlapped by the front portion of the article. In some embodiments of this article, the second mechanical fasteners are dimensioned across a width of the article to prevent the formation of attachment points other than behind the transverse center plane of the article.

In another embodiment, a disposable absorbent article of the present invention defines a front portion, a rear portion and a crotch portion connecting the front and rear portions and having opposed longitudinal side edges. The article comprises an outer cover, a liquid-pervious body-side liner, and an absorbent material located between the outer cover and the body-side liner. A pair of opposed ears is located on the rear portion, the ears being adapted, in use, to overlap with the front portion of the article to form overlapped portions, but not to overlap one another. Attachment means is provided for attaching the overlapped portions of the ears to the front portion to form attachment points. The attachment points are located on a side of the article behind a transverse center plane of the article and within about 2.5 inches (6.4 centimeters) of the transverse center plane. A waist elastic member is attached to at least one of the front portion or the rear portion. Leg elastic members are attached to the crotch portion adjacent the opposed longitudinal side edges. The attachment means is constituted solely by first mechanical fasteners on a body side of the ears and second mechanical fasteners on the front portion. The first mechanical fasteners are hook members of hook and loop fasteners and the second mechanical fasteners are loop members of hook and loop fasteners, the hook members being adapted to releasably engage respective loop members to hold the ears overlapped with the front portion on the outside of the front portion. The article lacks any means other than the hook members of the first mechanical fasteners and the loop members of the second mechanical fasteners for holding the overlapped portions of the article in position. A pair of front ears is located on the front portion. The front ears have outer fastener-free regions disposed laterally outward of the absorbent material and the leg elastic members. The fastener-free regions are adapted, in use, to extend rearward past the transverse center plane and to be overlapped by the rear portion of the article. In some embodiments of this article, the first mechanical fasteners do not extend laterally outward beyond the ears on the rear portion, and the second mechanical fasteners are located laterally inward of the ears on the front portion. In some embodiments of this article the second mechanical fasteners are dimensioned across a width of the article to prevent the formation of attachment points other than behind the transverse center plane of the article.

In another embodiment, a disposable absorbent article of the present invention defines front portion, a rear portion and a crotch portion connecting the front and rear portions and having opposed longitudinal side edges. The article comprises an outer cover, a liquid-pervious body-side liner, and an absorbent material located between the outer cover and the body-side liner. A pair of opposed ears is located on the rear portion, the ears being adapted, in use, to overlap with the front portion of the article to form overlapped portions, but not to overlap one another. Attachment means is provided for attaching the overlapped portion of the ears to the front portion to form attachment points. The attachment points are located on a side of the article behind a transverse center plane of the article and within about 2.5 inches (6.4 centimeters) of the transverse center plane. A waist elastic member is attached to at least one of the front portion or the rear portion. Leg elastic members are attached to the crotch portion adjacent the opposed longitudinal side edges. The attachment means is constituted solely by first mechanical fasteners on a body side of the ears and second mechanical fasteners on the front portion. The first mechanical fasteners are hook members of hook and loop fasteners and the second mechanical fasteners are loop members of hook and loop fasteners. The hook members are adapted to releasably engage respective loop members to hold the ears overlapped with the front portion on the outside of the front portion. The article lacks any means other than the hook members of the first mechanical fasteners and the loop members of the second mechanical fasteners for holding the overlapped portions of the article in position. The first and second mechanical fasteners are configured such that when the article is laid flat on a surface, the hook members of each first mechanical fastener do not extend laterally outward beyond a respective ear. A pair of front ears is located on the front portion. The front ears have outer fastener-free regions disposed laterally outward of the absorbent material and the leg elastic members. The fastener-free regions are adapted, in use, to extend rearward past the transverse center plane and to be overlapped by the rear portion of the article. In some embodiments of this article, the first mechanical fasteners do not extend laterally outward beyond the ears on the rear portion, and the second mechanical fasteners are located laterally inward of the ears on the front portion. In some embodiments of this article the second mechanical fasteners are dimensioned across a width of the article to prevent the formation of attachment points other than behind the transverse center plane of the article.

Column 5, lines 24–28:

In the embodiment illustrated in FIG. 1, the diaper 10 further comprises a pair of opposed ears 40 located on the rear portion of the diaper 10. The ears 40 located on the rear portion 20 can be formed and attached as described above in connection with ears 26. As shown in FIGS. *1* and *2*, the rear ears 40 have outer fastener-free regions 40A disposed laterally outward of the absorbent material 16 and leg elastic members 32. When the diaper is in use (See FIGS. *4A–4C*), these regions 40A extend forward past the transverse center plane of the diaper (indicated at Y in FIG. *1*) and are overlapped by the front portion 18 of the diaper.

Column 8, line 66 to column 9, line 12:

FIG. 3 illustrates still a further embodiment of the present invention. As can be seen from reference to FIG. 3, hook members 34 can, alternatively, be located on rear ear 40, while loop members 36 are located on the outer surface of the front portion 18 of diaper 10. In such a situation, rather than having the front-to-back fastening illustrated on the diapers of FIGS. 1 and 2, FIG. 3 illustrates a diaper having a more traditional back-to-front fastening. Nonetheless, the opposed ears 40 located on the rear portion are adapted, in use, to overlap with the front portion of the article. The hook-and-loop members, for attaching the overlap portion of the ears 40 to the front portion 18, form attachment points. The attachment points are located on the side of the diaper behind a transverse center plane of the diaper. As further shown in FIG. 3, the front ears 26 have outer fastener-free regions 26A disposed laterally outward of the absorbent material 16 and leg elastic members 32. When the diaper is in use (see FIG. 5), these regions 26A extend rearward past the transverse center plane of the diaper and are overlapped by the rear portion 20 of the diaper.

THE DRAWING FIGURES HAVE BEEN CHANGED AS FOLLOWS:

FIG. 1: add designation 40A and lead line; shorten lead line from designation 40.

FIG. 2: (same changes as for FIG. 1), and adder right hand side Ref. # 40.

FIG. 3: add designations 26A and lead lines; shorten lead line from designation 26.

AS A RESULT OF REEXAMINATION, IT HAS BEEN DETERMINED THAT:

Claims 13, 15–24 and 30 are cancelled.

Claims 1–3 and 25 are determined to be patentable as amended.

Claims 4–12, 14, 26–29 and 31, dependent on an amended claim, are determined to be patentable.

New claims 32–44 are added and determined to be patentable.

1. A disposable absorbent article, said article defining a front portion, a rear portion and a crotch portion connecting the front and rear portions and having opposed longitudinal side edges, said article comprising:
    an outer cover;
    a liquid-pervious body-side liner;
    an absorbent material located between said outer cover and said body-side liner;
    a pair of opposed *front* ears located on said front portion, said *front* ears being adapted, in use, to overlap with said rear portion of said article to form overlapped portions, *but not to overlap one another*;
    attachment means for attaching said overlapped portions of said *front* ears to said rear portion to form attachment points *for attachment of said article about the waist of a wearer without the use of other means*, said attachment points being located on a side of said article behind a transverse center plane of said article and within about 2.5 inches (6.4 centimeters) of said transverse center plane, *said attachment means being configured to prevent formation of any attachment points other than behind said transverse center plane*;
    a waist elastic member attached to at least one of said front portion or said rear portion; [and]
    leg elastic members attached to said crotch portion adjacent said opposed longitudinal side edges; *and*
    *a pair of rear ears located on said rear portion, said rear ears having outer fastener-free regions disposed laterally outward of said absorbent material and said leg elastic members, said fastener-free regions being adapted, in use, to extend forward past said transverse center plane and to be overlapped by said front portion of the article.*

2. The absorbent article according to claim 1 wherein said front ears are non-integrally formed with said front portion.

3. The absorbent article according to claim 1 wherein said attachment means comprise a first mechanical fastener attached to [said ears] *each front ear* and adapted to releasably engage with a second mechanical fastener attached to said rear portion.

25. A disposable absorbent article, said article defining a front portion, a rear portion, and a crotch portion connecting the front and rear portions and having opposed longitudinal side edges, said article comprising:
    an outer cover;
    a liquid-pervious body-side liner;
    an absorbent material located between said outer cover and said body-side liner;
    a pair of opposed ears located on said front portion, said ears being adapted, in use, to overlap with said rear portion of said article, *but not to overlap one another*;
    [a] first mechanical [fastener] *fasteners* attached to said opposed ears;
    [a] second mechanical [fastener] *fasteners* attached to said outer cover in said rear portion and being configured to releasably engage with [said] *respective* first mechanical [fastener] *fasteners* to define attachment points *for attachment of said article about the waist of a wearer without the use of other means*; all of said attachment points being located behind a transverse center plane of said article and within about 2.5 inches (6.4 centimeters) of said transverse center plane, *said first and second mechanical fasteners being configured to prevent formation of any attachment points other than behind said transverse center plane*; [and]
    leg elastic members attached to said crotch portion adjacent said opposed longitudinal side edges; *and*
    *a pair of rear ears located on said rear portion, said rear ears having outer fastener-free regions disposed laterally outward of said absorbent material, said fastener-free regions being adapted, in use, to extend forward past said transverse center plane and to be overlapped by said front portion of the article.*

32. *A disposable absorbent article as set forth in claim 1 wherein said attachment means comprises hook members on said ears and loop members on said rear portion, said hook and loop members being adapted to releasably engage to attach the article to said wearer without the use of other fasteners, and wherein said loop members are dimensioned across a width of the article to prevent said formation of attachment points other than behind said transverse center plane.*

33. *The absorbent article according to claim 1 or claim 25 wherein said attachment means comprises a first mechanical fastener attached to each front ear on said front portion, said first mechanical fastener being oblong in the direction of a longitudinal central axis of the article.*

34. *A disposable absorbent article, said article defining a front portion, a rear portion and a crotch portion connecting the front and rear portions and having opposed longitudinal side edges, said article comprising:*
    *an outer cover;*
    *a liquid-pervious body-side liner;*
    *an absorbent material located between said outer cover and said body-side liner;*
    *a pair of opposed front ears located on said front portion, said front ears being adapted, in use, to overlap with said rear portion of said article to form overlapped portions, but not to overlap one another;*
    *attachment means for attaching said overlapped portions of said front ears to said rear portion to form attachment points, said attachment points being located on a side of said article behind a transverse center plane of said article and within about 2.5 inches (6.4 centimeters) of said transverse center plane;*
    *a waist elastic member attached to at least one of said front portion or said rear portion;*
    *leg elastic members attached to said crotch portion adjacent said opposed longitudinal side edges;*
    *wherein said attachment means is constituted solely by first mechanical fasteners on a body side of said front ears and second mechanical fasteners on said outer cover;* wherein said first mechanical fasteners are hook members of hook and loop fasteners and said second mechanical fasteners are loop members of hook and loop fasteners, the hook members being adapted to releasably engage respective loop members to hold the front ears overlapped with said rear portion on the outside of the rear portion, said article lacking any means other than the hook members of said first mechanical fasteners and the loop members of said second mechanical fasteners for holding said overlapped portions of the article in position;

wherein said first and second mechanical fasteners are configured such that when said article is laid flat on a surface, all of the hook members of each first mechanical fastener are positioned laterally outward beyond all of the loop members of a respective second mechanical fastener; and a pair of rear ears located on said rear portion, said rear ears having outer fastener-free regions disposed laterally outward of said absorbent material and said leg elastic members, said fastener-free regions being adapted, in use, to extend forward past said transverse center plane and to be overlapped by said front portion of the article.

35. A disposable absorbent article, said article defining a front portion, a rear portion and a crotch portion connecting the front and rear portions and having opposed longitudinal side edges, said article comprising:

an outer cover;

a liquid-pervious body-side liner;

an absorbent material located between said outer cover and said body-side liner;

a pair of opposed front ears located on said front portion, said front ears being adapted, in use, to overlap with said rear portion of said article to form overlapped portions, but not to overlap one another;

attachment means for attaching said overlapped portions of said front ears to said rear portion to form attachment points, said attachment points being located on a side of said article behind a transverse center plane of said article and within about 2.5 inches (6.4 centimeters) of said transverse center plane;

a waist elastic member attached to at least one of said front portion or said rear portion;

leg elastic members attached to said crotch portion adjacent said opposed longitudinal side edges;

wherein said attachment means is constituted solely by first mechanical fasteners on a body side of said front ears and second mechanical fasteners on said outer cover;

wherein said first mechanical fasteners are hook members of hook and loop fasteners and said second mechanical fasteners are loop members of hook and loop fasteners, the hook members being adapted to releasably engage respective loop members to hold the front ears overlapped with said rear portion on the outside of the rear portion, said article lacking any means other than the hook members of said first mechanical fasteners and the loop members of said second mechanical fasteners for holding said overlapped portions of the article in position;

wherein said first and second mechanical fasteners are configured such that when said article is laid flat on a surface, the hook members of each first mechanical fastener do not extend laterally outwardly beyond a respective ear; and a pair of rear ears located on said rear portion, said rear ears having outer fastener-free regions disposed laterally outward of said absorbent material and said leg elastic members, said fastener-free regions being adapted, in use, to extend forward past said transverse center plane and to be overlapped by said front portion of the article.

36. A disposable absorbent article as set forth in claim 34 or claim 35 wherein said second mechanical fasteners are dimensioned across a width of the article to prevent said formation of attachment points other than behind said transverse center plane.

37. A disposable absorbent article as set forth in claim 34 or claim 35 wherein said leg elastic members cause said rear portion to become cup shaped.

38. A disposable absorbent article as set forth in claim 37 wherein said waist elastic member is attached to said rear portion, and wherein said leg elastic members curve outward into the rear portion beyond said absorbent member and terminate short of the waist elastic member.

39. A disposable absorbent article as set forth in claim 34 or claim 35 wherein said leg elastic members curve outward into the rear portion and terminate within about 1 in. of respective second mechanical fasteners on said rear portion.

40. A disposable absorbent article according to claim 34 wherein said first mechanical fasteners do not extend laterally outward beyond the ears on said front portion, and wherein the second mechanical fasteners are located laterally inward of said outer fastener-free regions of the rear ears on said rear portion.

41. A disposable absorbent article, said article defining a front portion, a rear portion and a crotch portion connecting the front and rear portions and having opposed longitudinal side edges, said article comprising:

an outer cover;

a liquid-pervious body-side liner;

an absorbent material located between said outer cover and said body-side liner;

a pair of opposed rear ears located on said rear portion, said rear ears being adapted, in use, to overlap with said front portion of said article to form overlapped portions, but not to overlap one another;

attachment means for attaching said overlapped portions of said rear ears to said front portion to form attachment points, said attachment points being located on a side of said article behind a transverse center plane of said article and within about 2.5 inches (6.4 centimeters) of said transverse center plane;

a waist elastic member attached to at least one of said front portion or said rear portion;

leg elastic members attached to said crotch portion adjacent said opposed longitudinal side edges;

wherein said attachment means is constituted solely by first mechanical fasteners on a body side of said rear ears and second mechanical fasteners on said front portion;

wherein said first mechanical fasteners are hook members of hook and loop fasteners and said second mechanical fasteners are loop members of hook and loop fasteners, the hook members being adapted to releasably engage respective loop members to hold the rear ears overlapped with said front portion on the outside of the front portion, said article lacking any means other than the hook members of said first mechanical fasteners and the loop members of said second mechanical fasteners for holding said overlapped portions of the article in position;

wherein said first and second mechanical fasteners are configured such that when said article is laid flat on a surface, all of the hook members of each first mechanical fastener are positioned laterally outward beyond all of the loop members of a respective second mechanical fastener; and a pair of front ears located on said front portion, said front ears having outer fastener-free regions disposed laterally outward of said absorbent material and said leg elastic members, said fastener-free regions being adapted, in use, to extend rearward past said transverse center plane and to be overlapped by said rear portion of the article.

42. A disposable absorbent article, said article defining a front portion, a rear portion and a crotch portion connecting the front and rear portions and having opposed longitudinal side edges, said article comprising:

an outer cover;

a liquid-pervious body-side liner;

an absorbent material located between said outer cover and said body-side liner;

a pair of opposed rear ears located on said rear portion, said rear ears being adapted, in use, to overlap with said front portion of said article to form overlapped portions, but not to overlap one another;

attachment means for attaching said overlapped portions of said rear ears to said front portion to form attachment points, said attachment points being located on a side of said article behind a transverse center plane of said article and within about 2.5 inches (6.4 centimeters) of said transverse center plane;

a waist elastic member attached to at least one of said front portion or said rear portion;

leg elastic members attached to said crotch portion adjacent said opposed longitudinal side edges;

wherein said attachment means is constituted solely by first mechanical fasteners on a body side of said ears and second mechanical fasteners on said front portion;

wherein said first mechanical fasteners are hook members of hook and loop fasteners and said second mechanical fasteners are loop members of hook and loop fasteners, the hook members being adapted to releasably engage respective loop members to hold the rear ears overlapped with said front portion on the outside of the front portion, said article lacking any means other than the hook members of said first mechanical fasteners and the loop members of said second mechanical fasteners for holding said overlapped portions of the article in position; and wherein said first and second mechanical fasteners are configured such that when said article is laid flat on a surface, the hook members of each first mechanical fastener do not extend laterally outward beyond a respective ear; and a pair of front ears located on said front portion, said front ears having outer fastener-free regions disposed laterally outward of said absorbent material and said leg elastic members, said fastener-free regions being adapted, in use, to extend rearward past said transverse center plane and to be overlapped by said rear portion of the article.

43. A disposable absorbent article as set forth in claim 41 or claim 42 wherein said second mechanical fasteners are dimensioned across a width of the article to prevent said formation of attachment points other than behind said transverse center plane.

44. The absorbent article according to claim 41 or claim 42 said first mechanical fasteners do not extend laterally outward beyond the rear ears on said rear portion, and wherein the second mechanical fasteners are located laterally inward of the front ears on said front portion.

\* \* \* \* \*